US009186053B2

(12) United States Patent
Viola

(10) Patent No.: US 9,186,053 B2
(45) Date of Patent: Nov. 17, 2015

(54) METHODS OF USING LIGHT TO REPAIR HERNIA DEFECTS

(71) Applicant: Covidien LP, Mansfield, MA (US)

(72) Inventor: Frank J. Viola, Sandy Hook, CT (US)

(73) Assignee: Covidien LP, Mansfield, MA (US)

( * ) Notice: Subject to any disclaimer, the term of this patent is extended or adjusted under 35 U.S.C. 154(b) by 293 days.

(21) Appl. No.: 13/860,695

(22) Filed: Apr. 11, 2013

(65) Prior Publication Data

US 2013/0296657 A1 Nov. 7, 2013

Related U.S. Application Data

(60) Provisional application No. 61/641,974, filed on May 3, 2012.

(51) Int. Cl.
| | | |
|---|---|---|
| *A61B 1/06* | (2006.01) | |
| *A61B 17/00* | (2006.01) | |
| *A61F 2/00* | (2006.01) | |
| *A61B 19/00* | (2006.01) | |

(52) U.S. Cl.
CPC .............. *A61B 1/06* (2013.01); *A61B 17/00234* (2013.01); *A61B 19/5202* (2013.01); *A61B 19/5212* (2013.01); *A61F 2/0063* (2013.01); *A61B 2019/202* (2013.01); *A61B 2019/5206* (2013.01); *A61B 2019/5445* (2013.01); *A61F 2002/0072* (2013.01)

(58) Field of Classification Search
CPC ........ A61B 1/07; A61B 1/00165; A61B 1/06; A61B 19/5202

USPC ........ 600/2–343, 414–415, 424–429; 607/88, 607/90–93; 606/151, 153–155
See application file for complete search history.

(56) References Cited

U.S. PATENT DOCUMENTS

| | | | | |
|---|---|---|---|---|
| 3,272,204 | A * | 9/1966 | Artandi et al. ................. | 606/151 |
| 3,376,869 | A * | 4/1968 | Borysko ......................... | 606/151 |
| 4,562,832 | A * | 1/1986 | Wilder et al. ................. | 600/223 |
| 4,619,249 | A * | 10/1986 | Landry ........................ | 600/245 |
| 4,688,554 | A * | 8/1987 | Habib ........................... | 600/114 |
| 4,898,175 | A | 2/1990 | Noguchi | |
| 5,143,076 | A | 9/1992 | Hardy et al. | |
| 5,242,456 | A * | 9/1993 | Nash et al. ..................... | 606/142 |
| 5,269,753 | A * | 12/1993 | Wilk ............................. | 600/116 |
| 5,275,166 | A * | 1/1994 | Vaitekunas et al. ........... | 600/439 |
| 5,280,788 | A * | 1/1994 | Janes et al. ..................... | 600/476 |
| 5,290,217 | A * | 3/1994 | Campos .......................... | 600/37 |
| 5,337,736 | A * | 8/1994 | Reddy ........................... | 600/217 |
| 5,353,786 | A * | 10/1994 | Wilk ............................. | 600/249 |
| 5,383,477 | A * | 1/1995 | DeMatteis ..................... | 128/898 |

(Continued)

*Primary Examiner* — Eduardo C Robert
*Assistant Examiner* — Michelle C. Eckman

(57) ABSTRACT

A hernia repair method includes the step of identifying a hernia defect in a patient, the hernia defect having a size, a location, and a shape. The method involves positioning a dispensing instrument laparoscopically into the patient adjacent the hernia defect. According to one step, the method includes dispensing one or more light pipes from the dispensing instrument at predetermined locations. The method also involves advancing the one or more light pipes through the patient's skin. Another step includes coupling a light source to the one or more light pipes. The method also involves generating a pattern of light that indicates one or more of the size, the location, and the shape of the hernia defect. One step includes positioning a surgical patch adjacent the hernia defect in accordance with the pattern of light.

20 Claims, 9 Drawing Sheets

(56) References Cited

U.S. PATENT DOCUMENTS

| | | | |
|---|---|---|---|
| 5,433,721 A * | 7/1995 | Hooven et al. | 606/143 |
| 5,456,720 A * | 10/1995 | Schultz et al. | 623/23.64 |
| 5,517,997 A | 5/1996 | Fontenot | |
| 5,540,711 A * | 7/1996 | Kieturakis et al. | 606/192 |
| 5,607,443 A * | 3/1997 | Kieturakis et al. | 606/192 |
| 5,622,170 A | 4/1997 | Schulz | |
| 5,695,525 A * | 12/1997 | Mulhauser et al. | 606/151 |
| 5,713,869 A * | 2/1998 | Morejon | 604/174 |
| 5,730,756 A * | 3/1998 | Kieturakis et al. | 606/190 |
| 5,772,680 A * | 6/1998 | Kieturakis et al. | 606/190 |
| 5,807,387 A | 9/1998 | Druais | |
| 5,891,158 A | 4/1999 | Manwaring et al. | |
| 5,907,395 A | 5/1999 | Schulz et al. | |
| 5,972,007 A * | 10/1999 | Sheffield et al. | 606/151 |
| 5,987,349 A | 11/1999 | Schulz | |
| 5,989,269 A * | 11/1999 | Vibe-Hansen et al. | 606/151 |
| 6,004,337 A * | 12/1999 | Kieturakis et al. | 606/190 |
| 6,041,249 A | 3/2000 | Regn | |
| 6,096,049 A | 8/2000 | McNeirney et al. | |
| 6,138,681 A | 10/2000 | Chen et al. | |
| 6,193,653 B1 * | 2/2001 | Evans et al. | 600/210 |
| 6,251,110 B1 * | 6/2001 | Wampler | 606/49 |
| 6,257,241 B1 * | 7/2001 | Wampler | 128/898 |
| 6,286,514 B1 | 9/2001 | Lemelson | |
| 6,287,344 B1 * | 9/2001 | Wampler et al. | 623/23.72 |
| 6,293,282 B1 | 9/2001 | Lemelson | |
| 6,317,616 B1 | 11/2001 | Glossop | |
| 6,354,297 B1 * | 3/2002 | Eiseman | 128/898 |
| 6,416,486 B1 * | 7/2002 | Wampler | 601/2 |
| 6,442,409 B1 | 8/2002 | Peyman | |
| 6,442,416 B1 | 8/2002 | Schultz | |
| 6,447,527 B1 * | 9/2002 | Thompson et al. | 606/174 |
| 6,540,764 B1 * | 4/2003 | Kieturakis et al. | 606/190 |
| 6,569,172 B2 * | 5/2003 | Asculai et al. | 606/151 |
| 6,587,702 B1 * | 7/2003 | Ruchti et al. | 600/310 |
| 6,597,941 B2 | 7/2003 | Fontenot et al. | |
| 6,694,164 B2 | 2/2004 | Glossop | |
| 6,711,423 B2 | 3/2004 | Colvin, Jr. | |
| 6,750,311 B1 * | 6/2004 | Van Antwerp et al. | 528/77 |
| 6,873,867 B2 | 3/2005 | Vilsmeier | |
| 6,978,166 B2 | 12/2005 | Foley et al. | |
| 6,991,637 B2 * | 1/2006 | Crawley et al. | 606/151 |
| 7,040,807 B2 | 5/2006 | Scheuering | |
| 7,224,472 B2 | 5/2007 | Bauch et al. | |
| 7,297,153 B2 * | 11/2007 | Kieturakis et al. | 606/190 |
| 7,404,819 B1 * | 7/2008 | Darios et al. | 606/151 |
| 7,450,783 B2 * | 11/2008 | Talapov et al. | 382/286 |
| 7,728,868 B2 | 6/2010 | Razzaque et al. | |
| 7,751,865 B2 | 7/2010 | Jascob et al. | |
| 7,881,770 B2 | 2/2011 | Melkent et al. | |
| RE44,380 E * | 7/2013 | de la Torre et al. | 604/256 |
| 8,617,157 B2 * | 12/2013 | Craig | 606/41 |
| RE44,790 E * | 3/2014 | de la Torre et al. | 604/256 |
| 8,814,788 B2 * | 8/2014 | Gan | 600/206 |
| 2002/0099279 A1 * | 7/2002 | Pfeiffer et al. | 600/314 |
| 2004/0049251 A1 * | 3/2004 | Knowlton | 607/101 |
| 2004/0064019 A1 * | 4/2004 | Chang et al. | 600/180 |
| 2004/0204734 A1 * | 10/2004 | Wagner et al. | 606/190 |
| 2004/0220541 A1 * | 11/2004 | Solomon et al. | 604/66 |
| 2004/0236231 A1 * | 11/2004 | Knighton et al. | 600/476 |
| 2005/0004576 A1 * | 1/2005 | Benderev | 606/72 |
| 2005/0113798 A1 * | 5/2005 | Slater et al. | 604/508 |
| 2005/0216040 A1 * | 9/2005 | Gertner et al. | 606/151 |
| 2005/0216041 A1 * | 9/2005 | Okada et al. | 606/151 |
| 2005/0277900 A1 * | 12/2005 | Klein et al. | 604/318 |
| 2005/0288691 A1 | 12/2005 | Leiboff | |
| 2005/0288706 A1 * | 12/2005 | Widomski et al. | 606/213 |
| 2006/0069313 A1 * | 3/2006 | Couvillon et al. | 600/179 |
| 2006/0270908 A1 * | 11/2006 | Luloh et al. | 600/182 |
| 2006/0282105 A1 * | 12/2006 | Ford et al. | 606/151 |
| 2007/0073160 A1 * | 3/2007 | Imam | 600/476 |
| 2007/0088391 A1 * | 4/2007 | McAlexander et al. | 606/232 |
| 2007/0185506 A1 * | 8/2007 | Jackson | 606/151 |
| 2007/0260179 A1 * | 11/2007 | Sholev et al. | 604/103 |
| 2007/0270890 A1 * | 11/2007 | Miller | 606/151 |
| 2008/0033263 A1 * | 2/2008 | Marcinek et al. | 600/322 |
| 2008/0058836 A1 | 3/2008 | Moll et al. | |
| 2008/0065229 A1 * | 3/2008 | Adams | 623/23.75 |
| 2008/0081945 A1 * | 4/2008 | Toso et al. | 600/37 |
| 2008/0082078 A1 * | 4/2008 | Berlin | 604/521 |
| 2008/0109015 A1 * | 5/2008 | Chu et al. | 606/139 |
| 2008/0132753 A1 * | 6/2008 | Goddard | 600/37 |
| 2008/0132917 A1 * | 6/2008 | Mueller | 606/144 |
| 2008/0167546 A1 * | 7/2008 | Youmans et al. | 600/407 |
| 2009/0105728 A1 * | 4/2009 | Noda et al. | 606/139 |
| 2009/0171142 A1 * | 7/2009 | Chu | 600/37 |
| 2009/0187181 A1 | 7/2009 | Shadduck | |
| 2009/0192528 A1 * | 7/2009 | Higgins et al. | 606/151 |
| 2009/0192530 A1 * | 7/2009 | Adzich et al. | 606/151 |
| 2009/0210006 A1 * | 8/2009 | Cohen et al. | 606/232 |
| 2009/0216253 A1 * | 8/2009 | Bell et al. | 606/153 |
| 2009/0234370 A1 | 9/2009 | Haras | |
| 2009/0234379 A1 * | 9/2009 | Rehnke | 606/190 |
| 2010/0036393 A1 | 2/2010 | Unsworth | |
| 2010/0042091 A1 | 2/2010 | Shadduck | |
| 2010/0056928 A1 * | 3/2010 | Zuzak et al. | 600/476 |
| 2010/0104608 A1 * | 4/2010 | Abuzaina et al. | 424/400 |
| 2010/0145415 A1 * | 6/2010 | Dahm et al. | 607/88 |
| 2010/0168763 A1 | 7/2010 | Zhao et al. | |
| 2010/0191237 A1 | 7/2010 | Shadduck | |
| 2010/0274282 A1 * | 10/2010 | Olson | 606/228 |
| 2010/0280538 A1 * | 11/2010 | Perkins et al. | 606/185 |
| 2010/0286473 A1 * | 11/2010 | Roberts | 600/37 |
| 2010/0292724 A1 * | 11/2010 | Ravikumar et al. | 606/185 |
| 2010/0298953 A1 | 11/2010 | Holzman | |
| 2011/0009894 A1 | 1/2011 | Forsell | |
| 2011/0009897 A1 | 1/2011 | Forsell | |
| 2011/0032715 A1 * | 2/2011 | Beau et al. | 362/459 |
| 2011/0040311 A1 | 2/2011 | Levin et al. | |
| 2011/0077456 A1 * | 3/2011 | Drummond | 600/30 |
| 2011/0077668 A1 * | 3/2011 | Gordon et al. | 606/142 |
| 2011/0082442 A1 * | 4/2011 | Solovay et al. | 604/524 |
| 2011/0098700 A1 * | 4/2011 | Tamai et al. | 606/41 |
| 2011/0106113 A1 * | 5/2011 | Tavakkolizadeh et al. | 606/151 |
| 2011/0112573 A1 * | 5/2011 | Bloom | 606/213 |
| 2011/0130774 A1 * | 6/2011 | Criscuolo et al. | 606/151 |
| 2011/0208215 A1 * | 8/2011 | Modesitt et al. | 606/151 |
| 2011/0224704 A1 * | 9/2011 | Bailly et al. | 606/151 |
| 2011/0276090 A1 * | 11/2011 | Berndt et al. | 606/230 |
| 2011/0297161 A1 * | 12/2011 | Deitch | 128/834 |
| 2011/0319915 A1 * | 12/2011 | Viola | 606/151 |
| 2012/0004501 A1 * | 1/2012 | Beyer | 600/37 |
| 2012/0041263 A1 * | 2/2012 | Sholev | 600/118 |
| 2012/0071727 A1 * | 3/2012 | Hanson et al. | 600/249 |
| 2012/0116423 A1 * | 5/2012 | Gleiman et al. | 606/151 |
| 2012/0203273 A1 * | 8/2012 | Riskin et al. | 606/213 |
| 2012/0209301 A1 * | 8/2012 | Bell et al. | 606/151 |
| 2012/0209319 A1 * | 8/2012 | Bianco-Peled et al. | 606/213 |
| 2012/0215073 A1 * | 8/2012 | Sherman et al. | 600/249 |
| 2012/0232334 A1 * | 9/2012 | Bell et al. | 600/37 |
| 2012/0253339 A1 * | 10/2012 | Rick et al. | 606/33 |
| 2012/0289811 A1 * | 11/2012 | Viola et al. | 600/407 |
| 2012/0303011 A1 * | 11/2012 | Schaeffer | 606/16 |
| 2013/0041266 A1 * | 2/2013 | Rockrohr | 600/473 |
| 2013/0085337 A1 * | 4/2013 | Hess et al. | 600/157 |
| 2013/0096583 A1 * | 4/2013 | Mueller et al. | 606/148 |
| 2013/0190558 A1 * | 7/2013 | Alexander et al. | 600/37 |
| 2013/0190598 A1 * | 7/2013 | Sharonov et al. | 600/409 |
| 2013/0218075 A1 * | 8/2013 | Gertz et al. | 604/93.01 |
| 2013/0225936 A1 * | 8/2013 | Alexander et al. | 600/235 |
| 2013/0226037 A1 * | 8/2013 | Pinto et al. | 600/587 |
| 2013/0226156 A1 * | 8/2013 | Sharonov | 606/1 |
| 2013/0253387 A1 * | 9/2013 | Bonutti et al. | 601/46 |
| 2013/0296657 A1 * | 11/2013 | Viola | 600/249 |
| 2013/0303845 A1 * | 11/2013 | Skula et al. | 600/104 |
| 2014/0031665 A1 * | 1/2014 | Pinto et al. | 600/407 |
| 2014/0100431 A1 * | 4/2014 | Curcillo | 600/249 |
| 2014/0100604 A1 * | 4/2014 | Litvack et al. | 606/213 |
| 2014/0155711 A1 * | 6/2014 | Mitchell et al. | 600/309 |
| 2014/0187661 A1 * | 7/2014 | El Fray et al. | 522/33 |
| 2014/0194806 A1 * | 7/2014 | Belhe et al. | 604/8 |
| 2014/0213968 A1 * | 7/2014 | Vaccaro et al. | 604/97.03 |
| 2014/0236222 A1 * | 8/2014 | Tegels | 606/213 |
| 2014/0243872 A1 * | 8/2014 | Cordray | 606/192 |

(56) References Cited

U.S. PATENT DOCUMENTS

| | | | |
|---|---|---|---|
| 2014/0257027 A1* | 9/2014 | Palmisano et al. | 600/37 |
| 2014/0275775 A1* | 9/2014 | Jones et al. | 600/109 |
| 2014/0276627 A1* | 9/2014 | Jenkins et al. | 604/514 |
| 2014/0276996 A1* | 9/2014 | Sharonov | 606/151 |
| 2014/0277043 A1* | 9/2014 | Jenkins et al. | 606/170 |
| 2014/0309626 A1* | 10/2014 | Sargeant | 606/14 |
| 2015/0005805 A1* | 1/2015 | Kesten et al. | 606/196 |
| 2015/0018851 A1* | 1/2015 | Francois et al. | 606/144 |
| 2015/0031990 A1* | 1/2015 | Boctor et al. | 600/424 |
| 2015/0032135 A1* | 1/2015 | Gorman | 606/151 |
| 2015/0039027 A1* | 2/2015 | Broom et al. | 606/228 |
| 2015/0045818 A1* | 2/2015 | Kim et al. | 606/151 |
| 2015/0051642 A1* | 2/2015 | Broom et al. | 606/228 |
| 2015/0055094 A1* | 2/2015 | Boate et al. | 351/206 |
| 2015/0066078 A1* | 3/2015 | Broom et al. | 606/228 |
| 2015/0073445 A1* | 3/2015 | Griffin et al. | 606/151 |
| 2015/0073473 A1* | 3/2015 | Broom et al. | 606/228 |

* cited by examiner

METHODS OF USING LIGHT TO REPAIR HERNIA DEFECTS

CROSS REFERENCE TO RELATED APPLICATION

The present application claims the benefit of and priority to U.S. Provisional Application Ser. No. 61/641,974, filed on May 3, 2012, the entire contents of which are incorporated herein by reference.

BACKGROUND

1. Technical Field

The present disclosure relates to hernia repair methods. More particularly, the present disclosure relates to methods for positioning a surgical patch to a tissue site of a hernia using light.

2. Description of Related Art

A hernia is a protrusion of a tissue, structure, or part of an organ through injured muscle tissue or an injured membrane by which the tissue, structure, or organ is normally contained. Some examples of hernias include: abdominal hernias, diaphragmatic hernias and hiatal hernias (for example, paraesophageal hernia of the stomach), pelvic hernias, for example, obturator hernia, anal hernias, hernias of the nucleus pulposus of the intervertebral discs, intracranial hernias, and Spigelian hernias.

Hernias may be surgically repaired, and are principally repaired by pushing back, or "reducing", the herniated tissue, and then reinforcing the defect in injured muscle tissue (an operation called herniorrhaphy). Modern muscle reinforcement techniques involve placement of a surgical patch, such as a surgical mesh, near the injured tissue or defect to support the defect. The surgical patch is either placed over the defect (anterior repair) or under the defect (posterior repair).

A variety of different fixation devices are used to anchor the surgical patch to the tissue. For example, a needled suture may be passed through or around the tissue near the defect to hold the surgical patch in a position which spans the injured tissue. In other examples, staples, tacks, clips and pins are also known to be passed through or around the tissue near the defect to anchor the surgical patch in a position which spans the injured tissue.

When applying a surgical patch during minimally invasive surgery, it is imperative that the surgeon know the precise location, size and shape of the hernia defect in order to properly place the surgical patch. However, since the bounds of the hernia defect are generally internal, visibility is often limited and placement of the surgical patch can be cumbersome. Thus, a continuing need still exits to provide a means for facilitating the effectiveness of the placement of surgical patches used to surgically repair hernias.

SUMMARY

Accordingly, a hernia repair method includes the step of identifying a hernia defect in a patient, the hernia defect having a size, a location, and a shape. The method involves positioning a dispensing instrument laparoscopically into the patient adjacent the hernia defect.

According to one step, the method includes dispensing one or more light pipes from the dispensing instrument at predetermined locations. The light pipes may be fiber optic. The method may include the step of positioning the dispensing instrument adjacent a corner or an extreme of the hernia defect prior to dispensing the one or more light pipes.

The method also involves advancing the one or more light pipes through the patient's skin. The method may further include piercing the patient's skin with that one or more light pipes. The method may further comprise the step of advancing the one or more light pipes to a position immediately adjacent the hernia defect after advancing the one or more light pipes through the patient's skin.

The method may include the step of bundling a plurality of light pipes. Another step includes coupling a light source to the one or more light pipes. The method also involves generating a pattern of light that indicates one or more of the size, the location, and the shape of the hernia defect. The method further includes the step of forming an outline of the hernia defect, in vivo, with the pattern of light being formed from the positioning of the plurality of light pipes at the predetermined locations.

One step includes positioning a surgical patch adjacent the hernia defect in accordance with the pattern of light. According to one step, the method involves generating a pattern of light that can be visualized, ex vivo, through the surgical patch when the surgical patch is positioned over the hernia defect in vivo. According to one step, the method involves removing the one or more light pipes from the patient after positioning the surgical patch adjacent the hernia defect.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
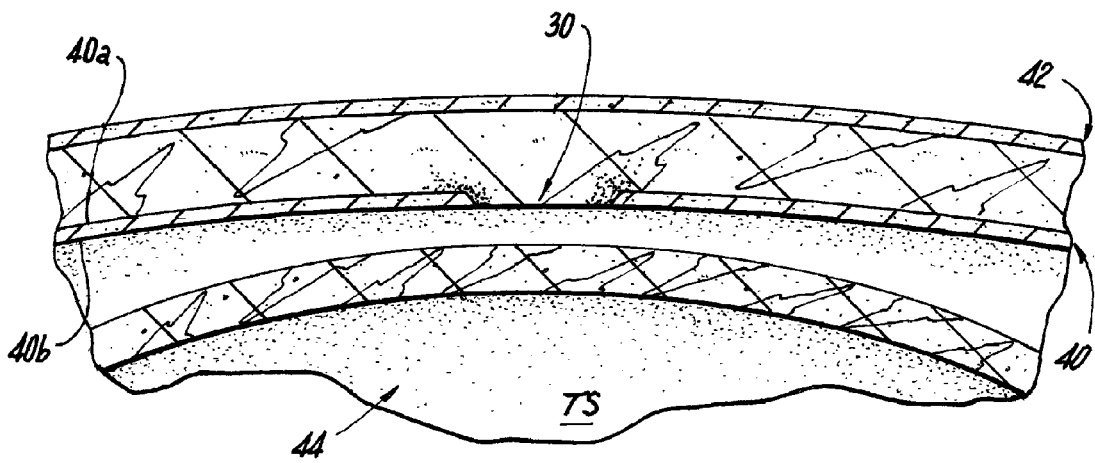
FIG. 1 is a cross-sectional view illustrating a tear in an abdominal wall.

The present disclosure relates to methods for surgeries such as transluminal and/or endoluminal placement of a surgical patch at a surgical site. As used herein the term "surgical patch" is used to refer to any type of patch for use in surgical procedures, such as, for example, meshes that can be attached to the abdominal wall. Although described herein with reference to a hernia surgical patch, the methods of the disclosure may be used in any surgical repair.

In the drawings and in the description that follows, the term "proximal," as is traditional, will refer to an end of a device that is closer to the user, while the term "distal" will refer to the end of the device that is farther from the user.

Figure 2:
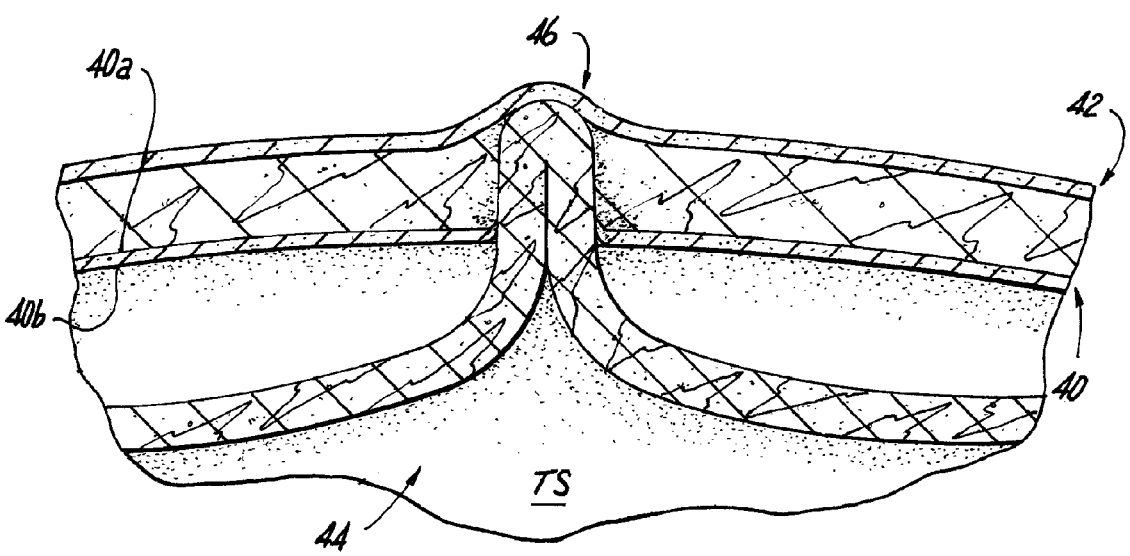
FIG. 2 is a cross-sectional view illustrating a ventral hernia.

Referring now in specific detail to the drawings, in which like numbers identify similar or identical elements, FIG. 1 illustrates a hernia that may involve a defect 30 such as a tear in the abdominal wall 40. The abdominal wall 40 is defined by an external side 40a and an internal side 40b. A surface tissue 42, which covers the external side 40a of abdominal wall 40, may or may not be immediately affected by this defect 30. An internal organ 44 located below the internal side 40b of the abdominal wall 40 may not protrude until some form of exertion or use of the muscle located at the abdominal wall 40 forces the internal organ 44 into the defect 30. Depending on the size and location of the defect 30, exertion may not be needed to cause the organ to protrude. As shown in FIG. 2, a hernia occurs when an internal organ 44 protrudes into the defect 30 of abdominal wall 40. Oftentimes the protrusion creates a bulge 46 in the surface tissue 42.

Figure 3:
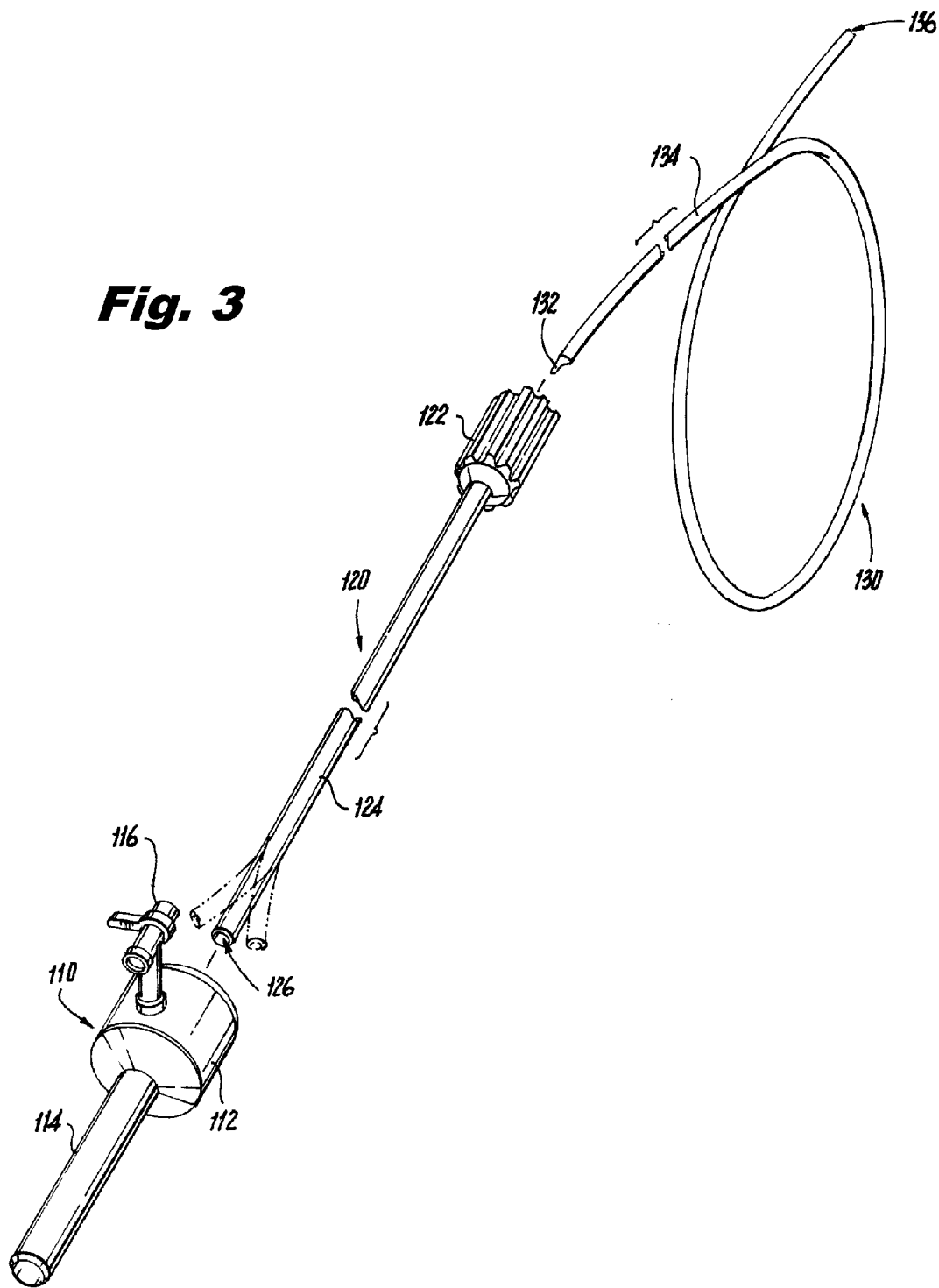
FIG. 3 is a perspective view of a hernia repair system in accordance with the present disclosure.

As depicted in FIG. 3, a hernia repair system 100 includes an access port 110, a dispensing instrument 120, and one or more light pipes 130.

The access port 110 includes a seal assembly 112 at a proximal end and cannula 114 at a distal end. The seal assembly 112 accommodates the dispensing instrument 120 in a substantially sealed relationship. The seal assembly 112 includes an insufflation valve 116 to selectively permit the passage of insufflation fluids therethrough to create a working space in an underlying tissue site.

The dispensing instrument 120 includes an actuation assembly 122 at a proximal end and a shaft 124 at a distal end. The shaft 124 extends from the actuation assembly 122. The shaft 124 defines a lumen 126 therethrough to accommodate the one or more light pipes 130. The shaft 124 is movable via the actuation assembly 122 to dispense the one or more light pipes 130 at predetermined locations within a patient. In particular, as illustrated in FIG. 3, the distal end of the shaft 124 may be rotatable, pivotable, and/or articulable to orient the distal end of the shaft 124 in a particular orientation relative to the hernia defect 30.

Each light pipe 130 includes a distal tip 132, which may be sharpened to pierce tissue, and an elongated member 134. The elongated member 134 may define a lumen 136 therethrough to permit the passage of light therethrough when coupled to a light source 150 (see FIG. 11). Alternatively, the elongated member 134 may include any suitable electrical and/or mechanical and/or chemical components configured to emit light from the distal end of the elongated member 134 (e.g., like a flashlight). The elongated member 134 may be rigid or flexible. The light pipes 130 may be fiber optic.

Figure 4:
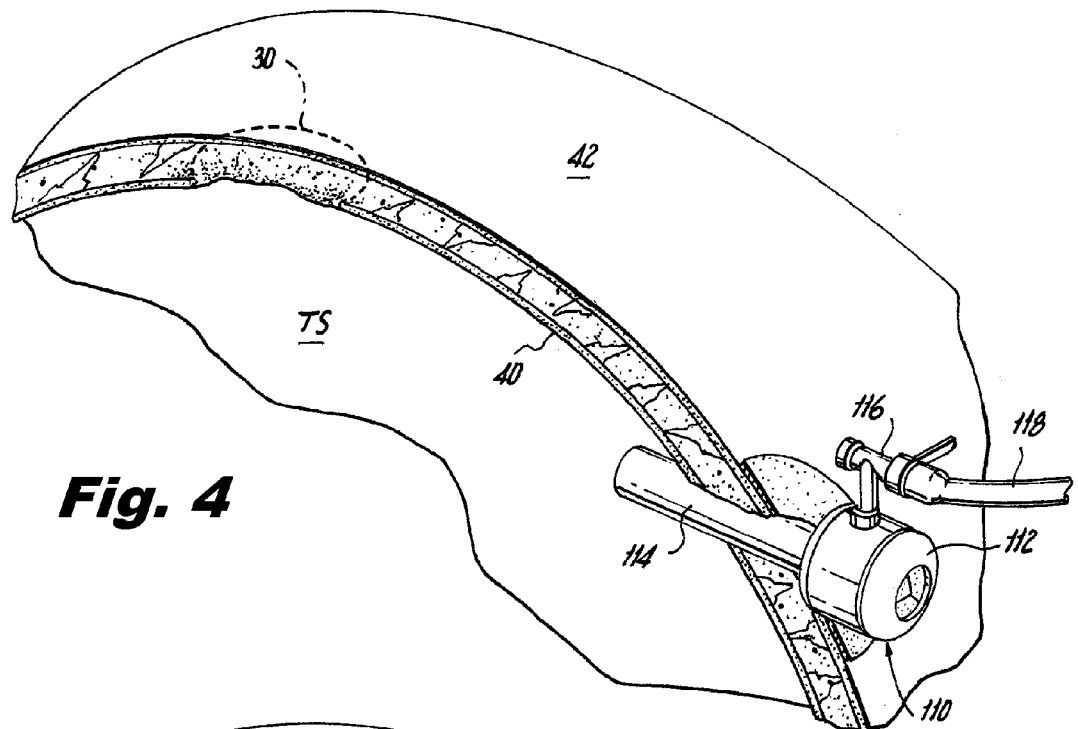
FIGS. 4-8 are progressive views illustrating a deployment of a light pipe of the hernia repair system of FIG. 3 into tissue.
Figure 5:
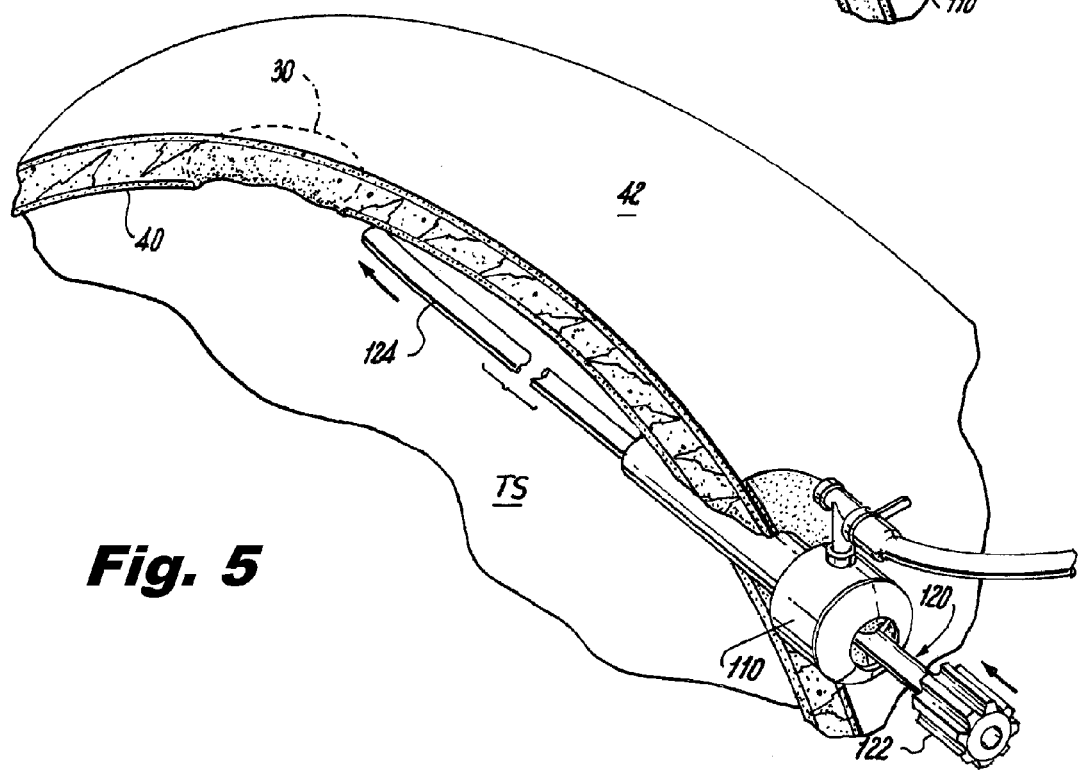
Figure 6:
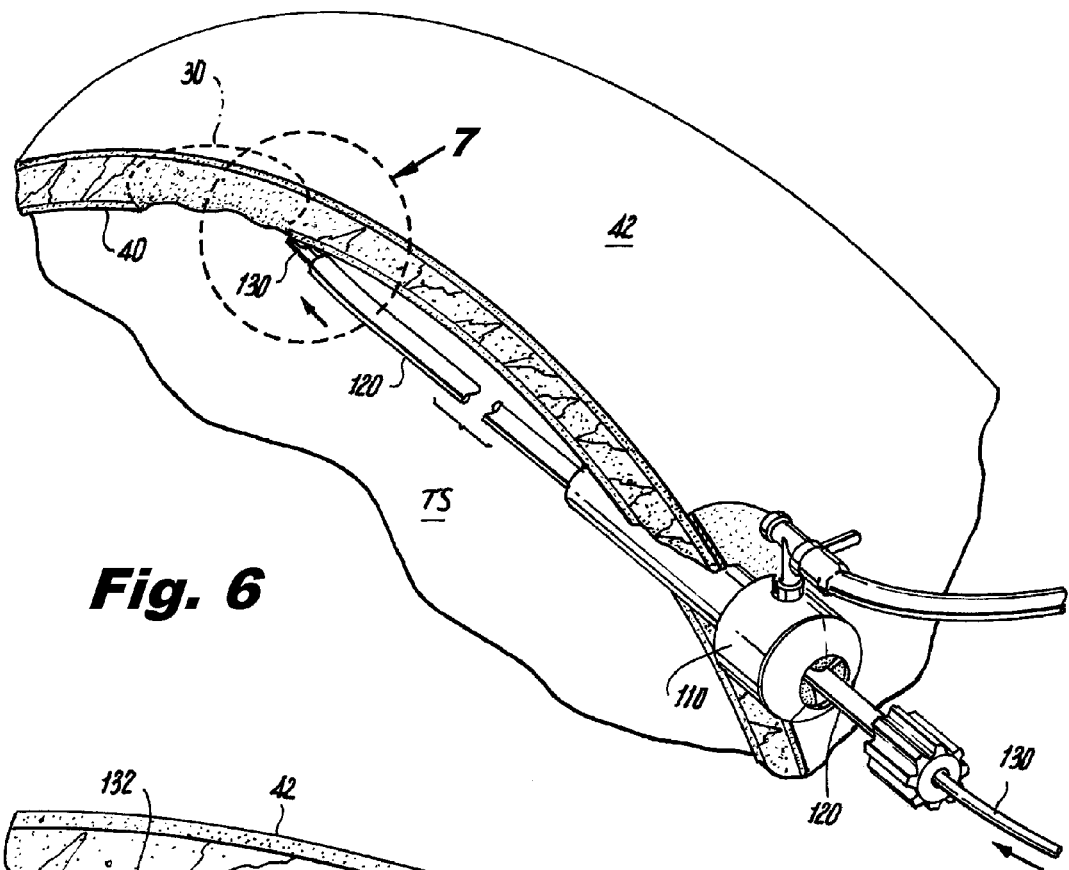
Figure 7:
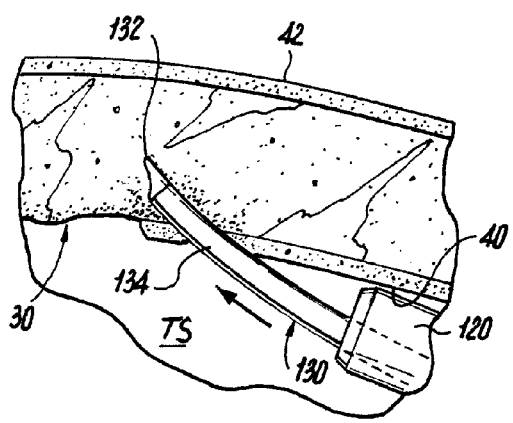
Figure 8:
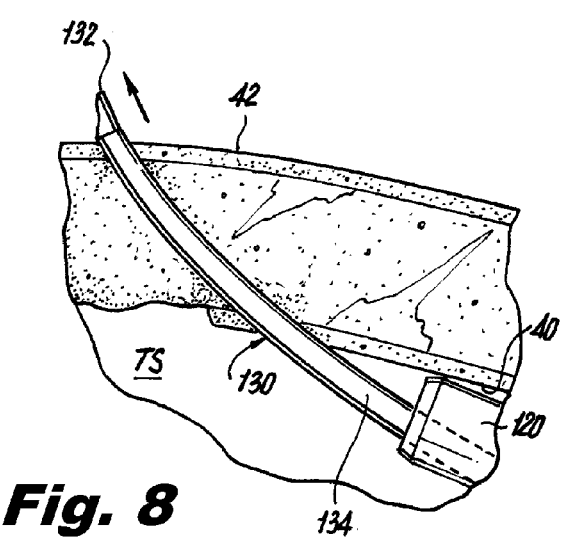
Figure 9:
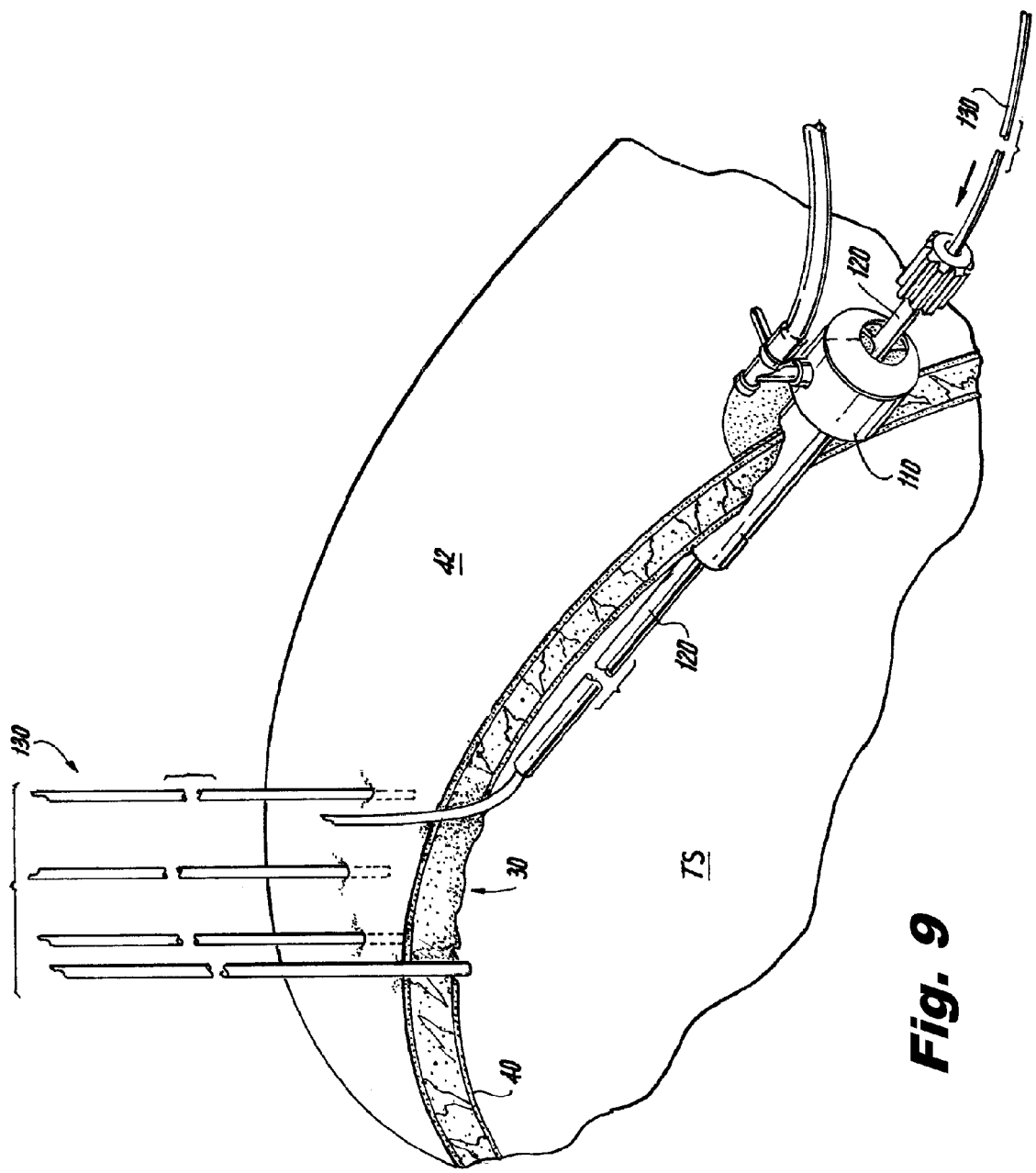
FIG. 9 is perspective view of a plurality of light pipes disposed in tissue after being deployed from the hernia repair system of FIG. 3.
Figure 10:
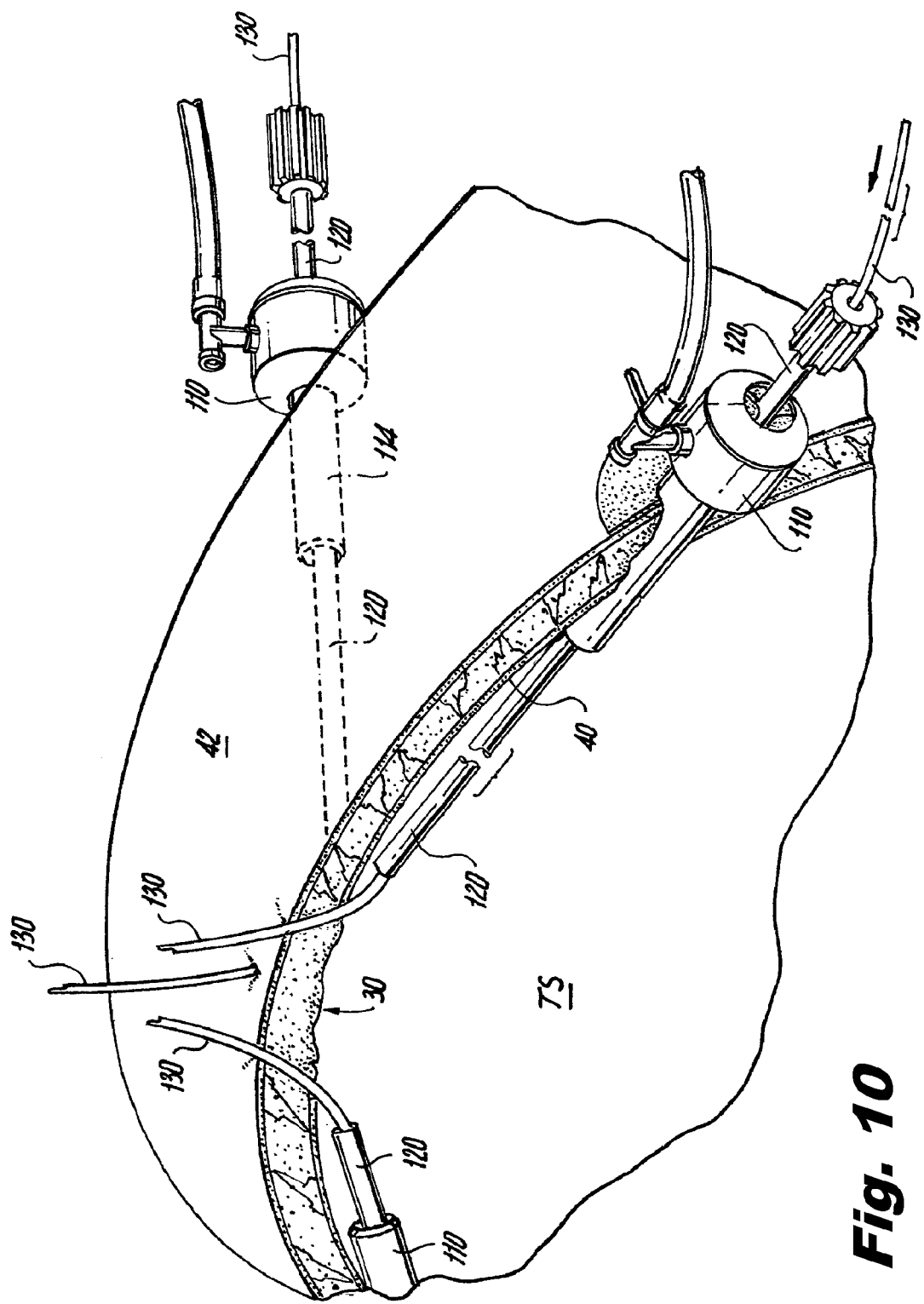
FIG. 10 is a perspective view of another embodiment of a hernia repair system deploying a plurality of light pipes in tissue in accordance with the present disclosure.

In use, a hernia defect 30 is identified in a patient. As can be appreciated, each hernia defect 30 has a particular size, location, and shape and therefore proper placement of a surgical patch 160 during minimally invasive surgery is facilitated when a practitioner can ascertain the size, location, and shape from an ex vivo location. Thus, in order to be able to perceive the hernia defect 30 from an ex vivo location, the practitioner inserts the access port 110, namely the cannula 114 into tissue adjacent the hernia defect 30 (see FIG. 4). With continued reference to FIGS. 4-5, the underlying tissue site "TS" may be insufflated when the insufflation valve 116 is coupled to an insufflation source 118 to create a working space. In this respect, the practitioner may then laparoscopically advance the dispensing instrument 120 into the patient adjacent the hernia defect 30 to facilitate placement of one or more light pipes 30 in position about the hernia defect 30, which is best depicted in FIG. 5. As depicted in FIG. 10, any number of access ports 110 and/or dispensing instruments 120 may be used to position the one or more light pipes 130 in tissue. In some modes of operation, the practitioner may even directly laparoscopically advance the one or more light pipes 30 through the access port 110 or directly laparoscopically advance the one or more light pipes 30 through an incision (without the access port 110) by virtue of the sharpened distal tip 132, where appropriate.

Turning now to FIGS. 6-9, one or more light pipes 130 may then be dispensed from the dispensing instrument 120 at predetermined locations about the hernia defect 30 to create a pattern about the defect 30 that is commensurate with the size, location, orientation and/or shape of the defect 30. For example, the dispensing instrument 120 may be positioned adjacent one or more corners and/or extremes of the hernia defect 30 prior to dispensing the one or more light pipes 130 to generate the pattern. The one or more light pipes 130 can then be dispensed with sufficient force to pierce and advance through the patient's skin, e.g. surface tissue 42. The one or more light pipes 130 may include sharpened tips 132 to further facilitate the penetration of the patient's skin. After the ends, e.g., the sharpened tips 132 are positioned so that they extend externally, the one or more light pipes 130 may be advanced to a position immediately adjacent the hernia defect 30 or the abdominal wall 40. In this respect, the one or more light pipes 130 may be pulled proximally through the pierced skin until they are positioned snug against the hernia defect 30 or the abdominal wall 40, depending upon the desired position.

Once in the snug position, the one or more light pipes 130 are most suitably configured in the pattern. The pattern may extend along the defect 30 and/or along an area immediately adjacent the defect 30. The pattern may have any suitable geometry, size, etc. for facilitating the placement of a surgical patch 160 adjacent the defect 30.

Figure 11:
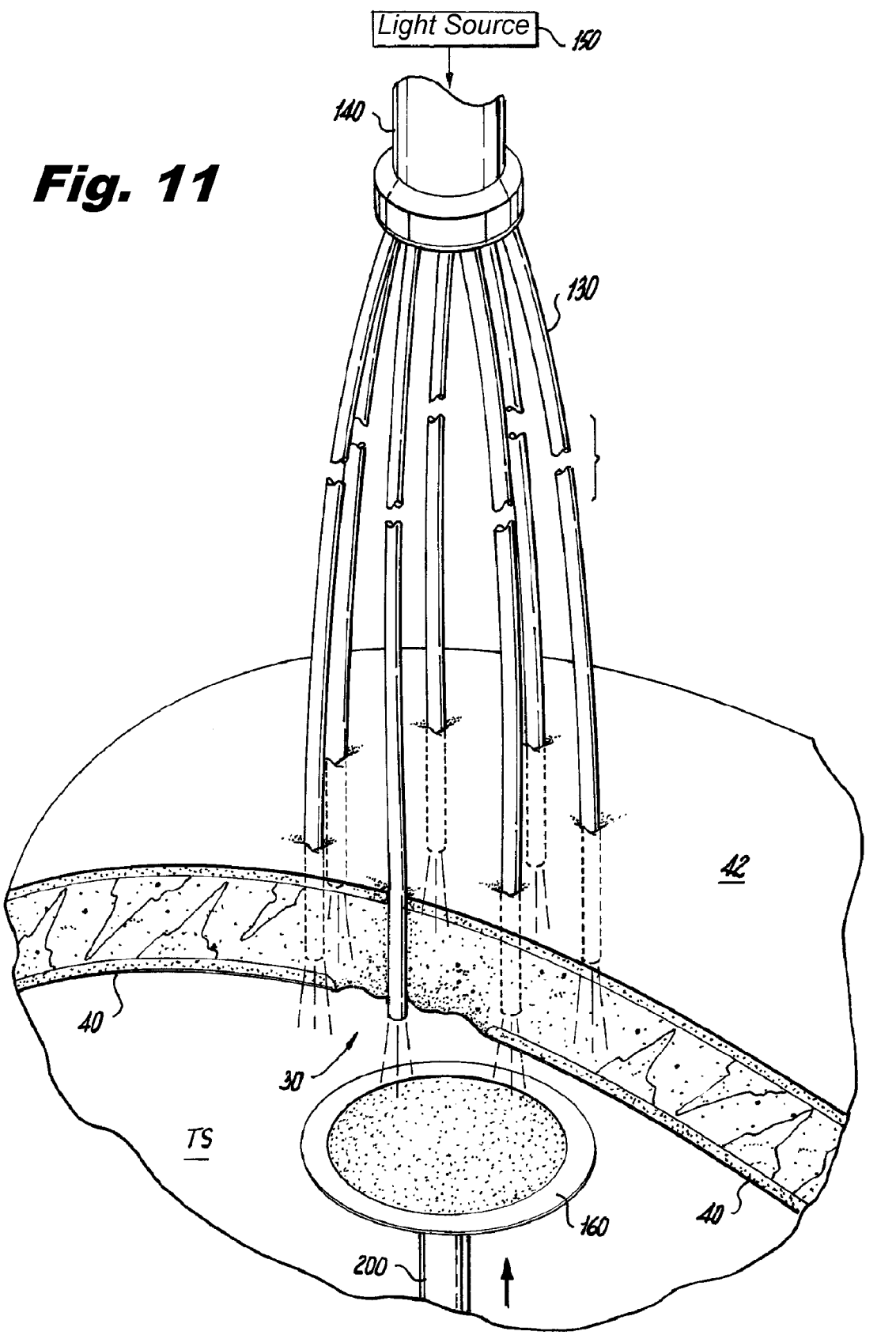
FIGS. 11-13 are progressive views illustrating a surgical patch being positioned adjacent a hernia defect with the aid of a plurality of light pipes in accordance with the present disclosure.
Figure 12:
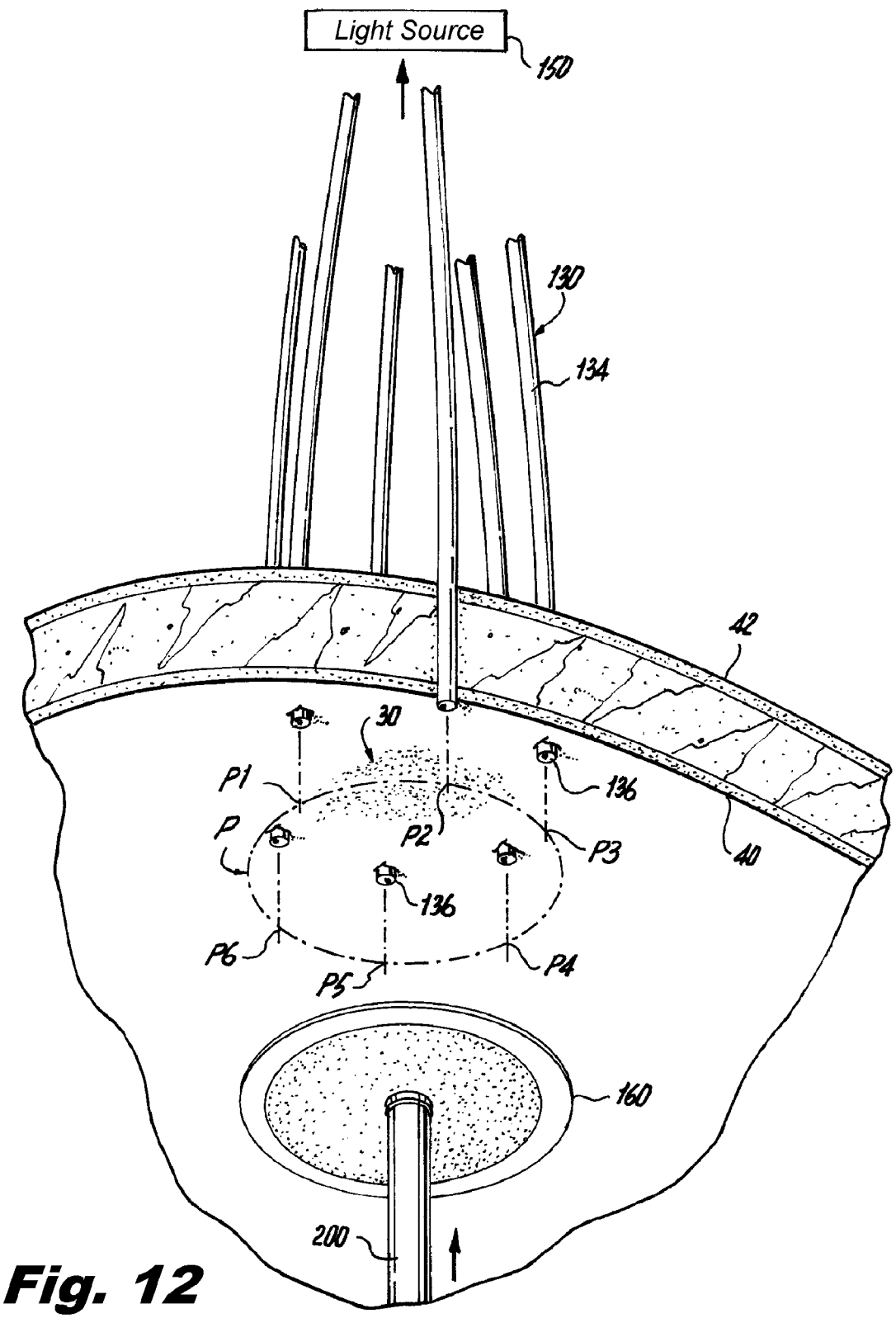
Figure 13:
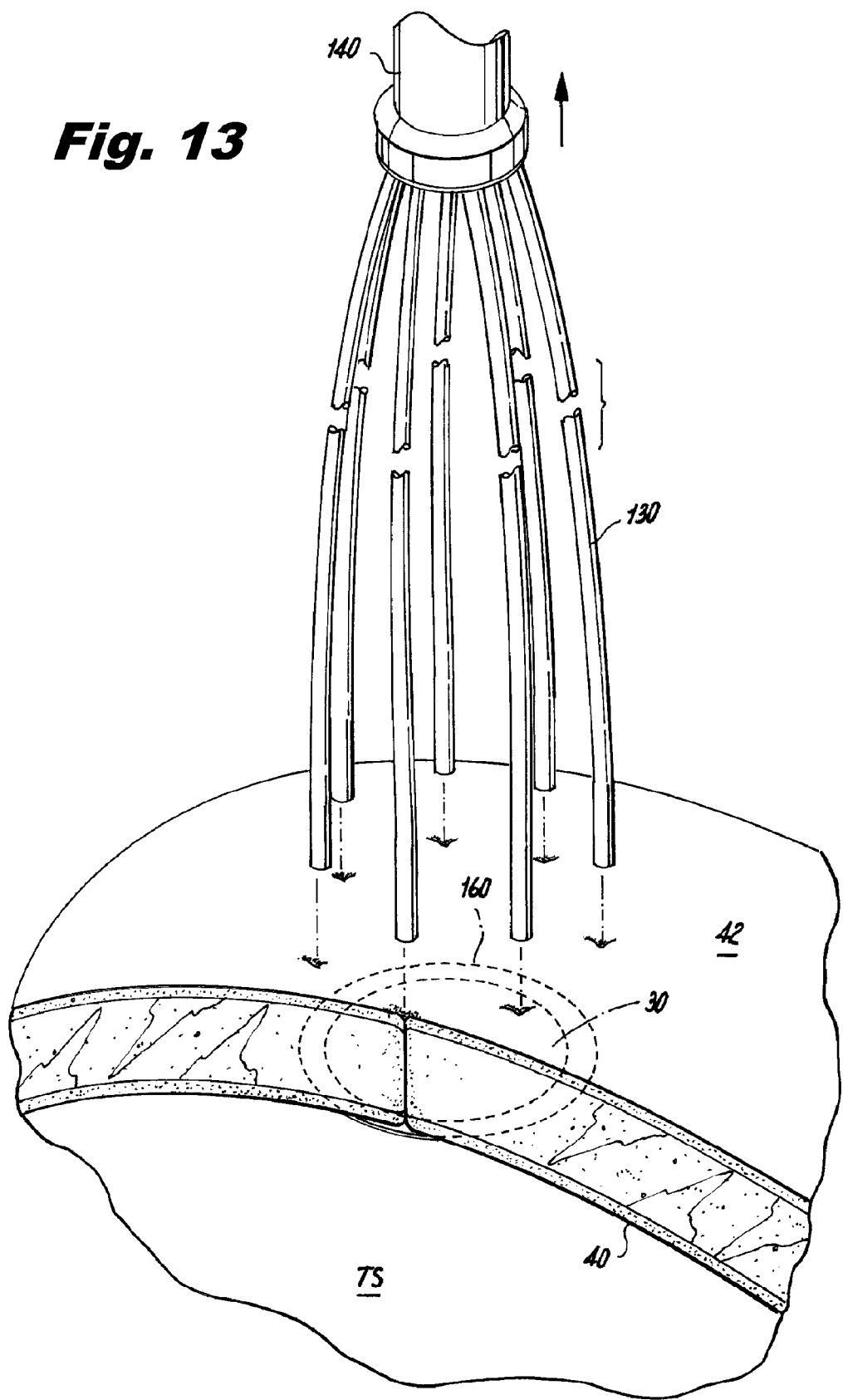

As illustrated in FIGS. 11-13, when the one or more light pipes 130 are coupled to a light source 150 or are otherwise adapted to emit light (e.g., selectively via a switch coupled to the one or more light pipes or autonomously by fluorescent chemicals or the like), one or more points of light are formed about the defect 30 corresponding to the pattern to indicate the size, location, orientation and/or shape of the defect 30.

With reference to FIG. 11, when there is a plurality of light pipes 130, the plurality may be bundled together via a bundling member 140. The light source 150 may then be coupled to the one or more light pipes 130, either individually, collectively, or by groups of light pipes 130. The bundling member 140 may include a light source 150. As depicted in FIG. 12, the light source 150 generates the pattern of light "P" via points of light P1, P2, P3, P4, P5, P6, etc. that indicate the size, the location, the orientation and/or the shape of the hernia defect 30. In this regard, the light emitted from the light source 150 will form an outline of the hernia defect 30, in vivo, so as to be viewable ex vivo so that the surgical patch 160 may be positioned adjacent the hernia defect 30 with any suitable instrument 200 (e.g., a grasper) in accordance with the outline/pattern of light. As can be appreciated, when the surgical patch 160 is positioned in vivo over the hernia defect 30, the generated pattern of light can be visualized, ex vivo, through the surgical patch 110 and the tissue. After the surgical patch 160 is placed in a desired position adjacent the hernia defect 30, the surgical patch 160 may be secured to the defect 30 by any suitable means (e.g., glue, tack, staple, suture, etc.) and the one or more light pipes 130 may then be removed from the patient either individually, collectively, or by groups of light pipes 130 (see FIG. 13).

The presently disclosed surgical patch may be any type of patch for use in surgical repair and suitable for use in situ. The surgical patch may be any suitable shape (i.e., circular, non-circular, etc.) and may include one or more layers. The surgical patch may be made of multiple fibers, or may be made of a single fiber. The fibers may be a monofilament or multifilament.

The fibers forming the presently disclosed patch may be made from a natural material or a synthetic material. The fibers may be biodegradable or non-biodegradable. Any combination of natural, synthetic, biodegradable and non-biodegradable materials may be used to form the fibers. The term "biodegradable" as used herein is defined to include both bioabsorbable and bioresorbable materials. By biodegradable, it is meant that the materials decompose, or lose structural integrity under body conditions (e.g. enzymatic degradation or hydrolysis) or are broken down (physically or chemically) under physiologic conditions in the body such that the degradation products are excretable or absorbable by the body.

The surgical patch of the present disclosure may be formed using any method suitable to forming patch structures, including but not limited to knitting, weaving, non-woven techniques, and the like. Suitable techniques for making the surgical patch are within the purview of those skilled in the art.

The surgical patch may be any shape or size suitable for covering the herniated area and securing the patch to surrounding tissue. The surgical patch may be preformed to a certain size, such as, for example, a 9 cm diameter round patch or 50 cm×50 cm square patch. In embodiments, the surgical patch may be cut to a particular size and shape as needed.

In addition, the surgical patch of the present disclosure may be rolled, folded, or otherwise oriented so that the surgical patch forms a shape more suitable for placement adjacent a hernia defect.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A hernia repair method, comprising:
   identifying a hernia defect in a patient, the hernia defect having a size, a location, and a shape;
   positioning a dispensing instrument laparoscopically into the patient adjacent the hernia defect;
   dispensing leading and trailing ends of a first light pipe from a leading end of the dispensing instrument at a predetermined location within the patient to separate the first light pipe from the dispensing instrument;
   advancing the leading end of the first light pipe through the patient's skin;
   coupling a light source to the leading end of the first light pipe;
   generating a pattern of light with the first light pipe that indicates at least one of: the size, the location, or the shape of the hernia defect; and
   positioning a surgical patch adjacent the hernia defect in accordance with the pattern of light.

2. The hernia repair method of claim 1, further comprising positioning the dispensing instrument adjacent a corner or a periphery of the hernia defect prior to dispensing the first light pipe.

3. The hernia repair method of claim 1, further comprising advancing the trailing end of the first light pipe to a position immediately adjacent the hernia defect after advancing the leading end of the first light pipe through the patient's skin.

4. The hernia repair method of claim 1, further comprising dispensing a second light pipe from the dispensing instrument.

5. The hernia repair method of claim 4, further comprising bundling the first and second light pipes.

6. The hernia repair method of claim 1, further comprising generating the pattern of light so that the pattern of light can be visualized, ex vivo, through the surgical patch when the surgical patch is positioned over the hernia defect in vivo.

7. The hernia repair method of claim 1, wherein the first light pipe is a fiber optic light pipe.

8. The hernia repair method of claim 1, further comprising removing the first light pipe from the patient after positioning the surgical patch adjacent the hernia defect.

9. The hernia repair method of claim 1, wherein coupling the light source to the leading end of the first light pipe includes transmitting light from the light source from the leading end of the first light pipe to the trailing end of the first light pipe so that light can exit from the trailing end of the first light pipe into the patient.

10. A hernia repair method, comprising:
    identifying a hernia defect in a patient, the hernia defect having a size, a location, and a shape;
    positioning a dispensing instrument laparoscopically into the patient adjacent the hernia defect;
    dispensing leading and trailing ends of a first light pipe from a leading end of the dispensing instrument at a predetermined location within the patient to separate the first light pipe from the dispensing instrument;
    piercing the patient's skin with the leading end of the first light pipe to cut through the patient's skin from an internal surface of the patient's skin to an external surface of the patient's skin, the leading end of the first light pipe being sharpened;
    advancing the leading end of the first light pipe through the patient's skin;
    coupling a light source to the leading end of the first light pipe;
    generating a pattern of light with the first light pipe that indicates at least one of: the size, the location, or the shape of the hernia defect; and
    positioning a surgical patch adjacent the hernia defect in accordance with the pattern of light.

11. The hernia repair method of claim 10, further comprising maintaining the trailing end of the first light pipe positioned within the patient after the leading end of the first light pipe is pierced through the internal and external surfaces of the patient's skin and positioned externally of the patient.

12. The hernia repair method of claim 10, further comprising positioning the dispensing instrument adjacent a corner or a periphery of the hernia defect prior to dispensing the first light pipe.

13. The hernia repair method of claim 10, further comprising advancing the trailing end of the first light pipe to a position immediately adjacent the hernia defect after advancing the leading end of the first light pipe through the patient's skin.

14. The hernia repair method of claim 10, further comprising dispensing a second light pipe from the dispensing instrument.

15. The hernia repair method of claim 14, further comprising generating the pattern of light with the first and second light pipes and positioning the first and second light pipes at predetermined locations within the patient to form an outline of the hernia defect in vivo.

16. The hernia repair method of claim 14, further comprising bundling the first and second light pipes.

17. The hernia repair method of claim 10, further comprising generating the pattern of light so that the pattern of light can be visualized, ex vivo, through the surgical patch when the surgical patch is positioned over the hernia defect in vivo.

18. The hernia repair method of claim 10, wherein the first light pipe is a fiber optic light pipe.

19. The hernia repair method of claim 10, further comprising removing the first light pipe from the patient after positioning the surgical patch adjacent the hernia defect.

20. The hernia repair method of claim 10, wherein coupling the light source to the leading end of the first light pipe includes transmitting light from the light source from the leading end of the first light pipe to the trailing end of the first light pipe so that light can exit from the trailing end of the first light pipe into the patient.

* * * * *